United States Patent [19]

Zuckerman

[11] Patent Number: 5,626,134

[45] Date of Patent: *May 6, 1997

[54] METHOD AND APPARATUS FOR THE MEASUREMENT OF ANALYTE CONCENTRATION LEVELS BY THE STEADY-STATE DETERMINATION OF FLUORESCENCE LIFETIME

[76] Inventor: Ralph Zuckerman, 226 W. Rittenhouse Square, Philadelphia, Pa. 19103

[*] Notice: The term of this patent shall not extend beyond the expiration date of Pat. No. 5,515,864.

[21] Appl. No.: 425,757

[22] Filed: Apr. 20, 1995

Related U.S. Application Data

[63] Continuation-in-part of Ser. No. 231,191, Apr. 21, 1994, Pat. No. 5,515,864.
[51] Int. Cl.$^6$ ............................................. A61B 5/00
[52] U.S. Cl. ........................... 128/633; 128/634; 356/41
[58] Field of Search ................................... 128/633, 634, 128/665; 356/41; 250/461.1

[56] References Cited

U.S. PATENT DOCUMENTS

| | | | |
|---|---|---|---|
| 4,115,699 | 9/1978 | Mizuta et al. | 250/461 |
| 4,476,870 | 10/1984 | Peterson et al. | |
| 4,579,430 | 4/1986 | Bille | |
| 4,810,655 | 3/1989 | Khalil et al. | |
| 4,947,850 | 8/1990 | Vanderkooi et al. | |
| 5,039,219 | 8/1991 | James et al. | |
| 5,120,510 | 6/1992 | Gourley et al. | 128/634 |

(List continued on next page.)

OTHER PUBLICATIONS de Coo, F.A., Zonnenberg, B.A., and Trap, N.H., "Prolonged Normothermic Perfusion of the Isolated Bovine Eye: Initial Results", Curr. Eye Res., 12(4): 293–301 (Apr. 1993).

Vanderkooi, J. et al., "An Optical Method for Measurement of Dioxygen Concentration Based Upon Quenching of Phosphorescence", J. Biol. Chem. 262(12); 5476–5482 (Apr. 1987).

*Primary Examiner*—Angela D. Sykes
*Assistant Examiner*—Eric F. Winakur
*Attorney, Agent, or Firm*—William H. Eilberg

[57] ABSTRACT

The use of luminescent probe substances is detailed in methods and an apparatus for the determination of the concentration and distribution in space and time of numerous analytes of biologic and physical import in vivo and in vitro by the steady-state determination of luminescence lifetime. In the instance of analytes that quench excited states, a fluorophore whose excited state is quenched by the analyte in question is free to undergo Brownian rotation alone or when conjugated to a carrier molecule within a medium of suitable viscosity. The analysis medium is irradiated with continuous linearly polarized light at a wavelength strongly absorbed by the fluorophore. The emitted luminescence is resolved into its vector components parallel and perpendicular to the plane of polarization of the excitation light, thereby permitting the calculation of the luminescence anisotropy of the irradiated specimen. The concentration of the quencher is determined by applying a mathematical function which relates the luminescence anisotropy of the fluorophore to the concentration of the quencher. For the determination of the concentration of substances which do not themselves quench excited states a known quantity of the analyte is conjugated to a quencher molecule or an energy transfer acceptor molecule and a competition reaction is set up in which the luminescently labelled substance and the unlabelled substance within the sample compete for sites on a labelled carrier molecule. To the extent that the concentration of unlabelled substance in the sample increases and displaces labelled material on the carrier molecule the luminescence lifetime of the carrier fluorophore will increase. The luminescence anisotropy is measured at the emission band of the luminescent label on the carrier molecule and the concentration of the substance under measurement is determined by applying an empirically determined mathematical function which relates luminescence anisotropy to the concentration of the analyte.

36 Claims, 4 Drawing Sheets

U.S. PATENT DOCUMENTS

| | | |
|---|---|---|
| 5,186,173 | 2/1993 | Zuckerman . |
| 5,251,633 | 10/1993 | Wunderling et al. .................. 128/634 |
| 5,281,825 | 1/1994 | Berndt et al. . |
| 5,317,162 | 5/1994 | Pinsky et al. . |
| 5,318,023 | 6/1994 | Vari et al. ................................ 128/633 |
| 5,341,805 | 8/1994 | Stavridi et al. .......................... 128/633 |
| 5,383,452 | 1/1995 | Buchert .................................... 128/633 |
| 5,495,850 | 3/1996 | Zuckerman ............................. 128/634 |
| 5,515,864 | 5/1996 | Zuckerman ............................. 128/633 |

METHOD AND APPARATUS FOR THE MEASUREMENT OF ANALYTE CONCENTRATION LEVELS BY THE STEADY-STATE DETERMINATION OF FLUORESCENCE LIFETIME

RELATED APPLICATIONS

This application is a continuation-in-part of pending application filed as application Ser. No. 08/231,191, filed on Apr. 21, 1994, now U.S. Pat. No. 5,515,864, entitled METHOD AND APPARATUS FOR THE IN VIVO MEASUREMENT OF OXYGEN CONCENTRATION LEVELS BY THE INDIRECT DETERMINATION OF FLUORESCENCE LIFETIME, the entire disclosure of which is incorporated by reference herein.

BACKGROUND OF THE INVENTION

Luminescence quenching is a well-established optical procedure for the determination of the concentrations of analytes which are themselves quenchers of excited states. The simplest and least expensive procedure for such determinations involves the use of fluorescence intensity measurements. However, such procedures require frequent recalibration due to photobleaching of the fluorophore, and may be inaccurate or imprecise due to light scattering within the medium and by the filtering effects of substances in the sample which absorb light at the excitation or emission wavelengths. Examples of fluorescence intensity procedures which suffer from some or all of the above deficiencies are U.S. Pat. No. 4,476,870 (Peterson et. al.) and U.S. Pat. No. 5,186,173 (Zuckerman) for the determination of dioxygen concentration levels. The determination of luminescence lifetime (decay) rather than intensity overcomes the deficiencies of intensity-based procedures. Luminescence lifetime is typically measured by one of two time-resolved procedures, viz., pulse fluorometry or phase modulation fluorometry. Examples of such approaches are U.S. Pat. No. 5,039,219 (James et. al.) in the case of pulse fluorometric procedures and U.S. Pat. No. 5,317,162 (Pinsky et. al.) as well as U.S. Pat. No. 5,281,825 (Berndt et. al.) in the case of phase modulation fluorometry. However, when applied to fluorophores with lifetimes in the nanosecond range the costs for implementing such techniques can be prohibitive, and have prevented their use in clinical laboratory instruments. That is, the cost of pulse lasers and gating devices such as microchannel plate intensifiers and photon counters for pulse fluorometry, and devices to modulate excitation light in the 10–100 MHz. range for phase systems have restricted such procedures to the research laboratory. Similarly, such direct lifetime systems suffer from a further deficiency in addition to high cost, i.e., they become increasingly less accurate as luminescence lifetime shortens with increasing concentrations of the quenching analyte.

In pending U.S. Pat. Ser. No. 08/231,191 (Zuckerman) a novel procedure for the indirect, steady-state determination of luminescence lifetime was disclosed for the case of the analyte dioxygen. The methodology, based upon the determination of luminescence anisotropy, overcomes the deficiencies in time-resolved determinations of luminescence lifetimes. In addition, to one skilled in the art it would be obvious that the method disclosed in the above noted pending patent application is a general methodology which may be applied to the determination of the concentration levels of numerous analytes of biologic and physical import. Herein, the general methodology is further detailed for the case of analytes which quench excited states, and a novel adaptation of this procedure is disclosed which allows the method to be extended to the measurement of concentrations of analytes which do not themselves quench excited states.

OBJECTS OF THE INVENTION

Accordingly, it is a general object of this invention to provide an apparatus and methods for the determination of the concentration and distribution in time and space of numerous substances of biologic and physical import, in vivo and in vitro, which quench excited states, the method being based upon the steady-state determination of luminescence lifetime.

It is a further object of this invention to provide an apparatus and methods for the determination of the concentration and distribution in time and space of numerous substances of biologic and physical import, in vivo and in vitro, which do not themselves quench excited states, the method again being based upon the steady-state determination of luminescence lifetime.

It is another object of this invention to provide a method for the determination of luminescence lifetimes which is equally precise and accurate for short as well as long luminescence lifetimes.

It is a further object of this invention to provide a method for the determination of analyte concentrations which is reproducible and accurate, and which may be implemented in a number of cost-effective configurations.

SUMMARY OF THE INVENTION

These and other objects of this invention are achieved by providing an apparatus and methods for the determination of the concentration and distribution of numerous substances of biologic and physical import, in vivo and in vitro, by means of the steady-state determination of luminescence lifetime. In the instance of analytes which quench excited states, a fluorophore whose excited state is quenched by the analyte in question is free to undergo Brownian rotation alone or when conjugated to a carrier molecule within a medium of suitable viscosity. The analysis medium is irradiated with continuous linearly polarized light at a wavelength strongly absorbed by the fluorophore. The emitted fluorescence is resolved into its vector components parallel and perpendicular to the plane of polarization of the excitation light, thereby permitting the calculation of the fluorescence anisotropy of the irradiated specimen. The concentration of the quencher (analyte) is determined by applying a mathematical function which relates the fluorescence anisotropy of the fluorophore to the concentration of the quencher. For the determination of the concentration of substances which do not themselves quench excited states a quantity of the substance under measurement is conjugated to a quencher molecule or an energy transfer acceptor molecule and a competition reaction is set up in which the luminescently labelled substance and the unlabelled substance within the sample compete for sites on a labelled carrier molecule. To the extent that the concentration of unlabelled substance in the sample increases and displaces labelled material on the carrier molecule the luminescence lifetime of the carrier fluorophore will increase. The luminescence anisotropy is measured at the emission band of the luminescent label on the carrier molecule and the concentration of the substance under measurement is determined by applying an empirically determined mathematical function which relates fluorescence anisotropy to the concentration of the analyte being measured.

BRIEF DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF PREFERRED EMBODIMENTS

Figure 1:
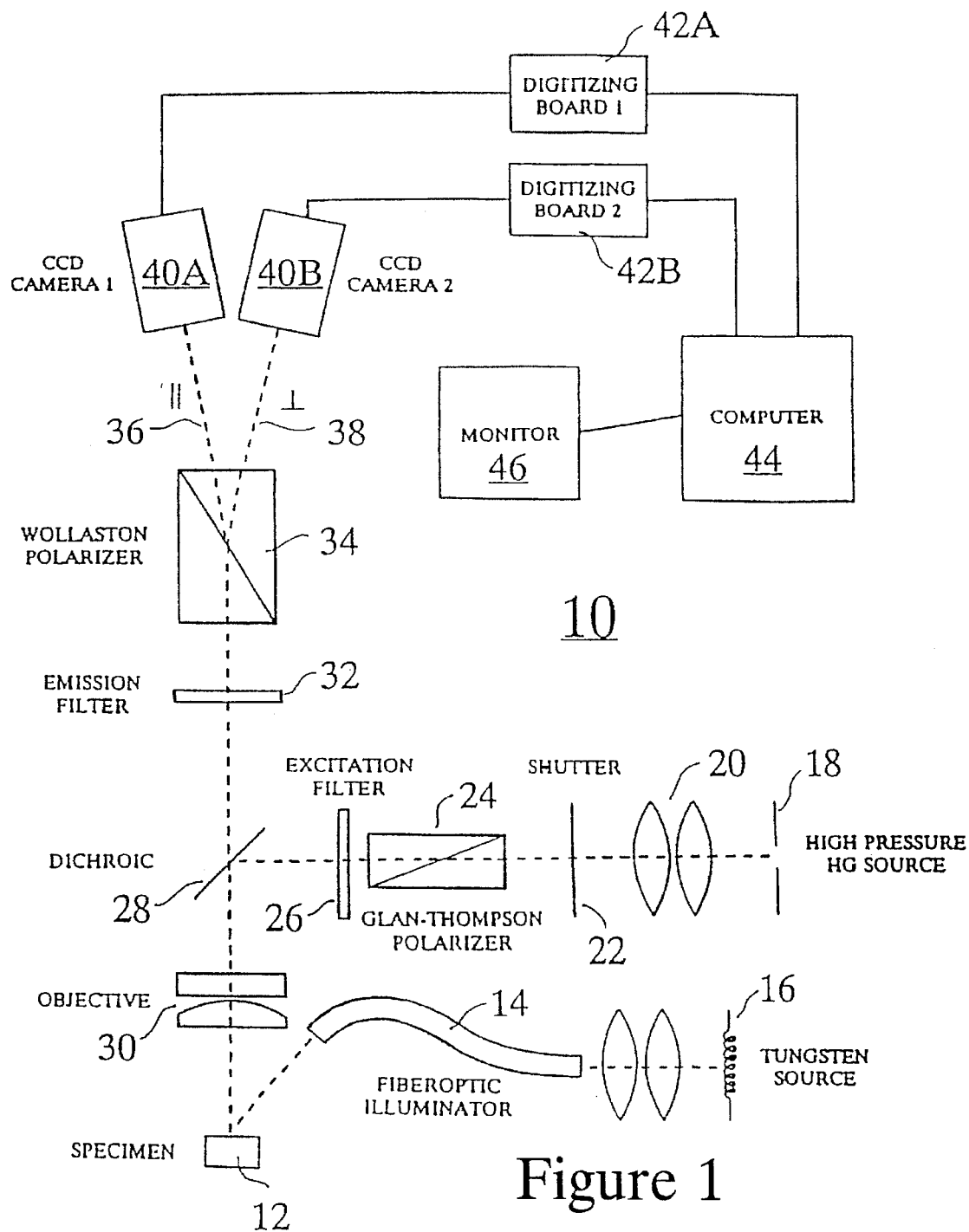
FIG. 1 is a schematic illustration of an imaging apparatus used to determine the topographic distribution of tissue and bodily fluid analyte concentration within an imaged specimen.

The present invention addresses several problems inherent in the prior art. The invention is based upon the well-accepted physical principle that absorption and emission of photons by fluorophores occur via electric dipole transition moments which have well-defined orientations within the molecular frame of the fluorophore. In a nonpolar solvent or lipid bilayer containing randomly oriented fluorophores only suitably oriented molecules can be excited by linearly polarized light, thus creating a nonequilibrium orientation of excited and fluorescing molecules. This anisotropy, and its rotational relaxation, are reflected in the polarization of the emitted light. The case of time-resolved fluorescence anisotropy induced by a pulse of linearly polarized light may be described by the following equation:

$$A(t) = A_o e^{-6\bar{R}t} \quad (1)$$

where A is fluorescence anisotropy, t is time of observation after pulsed excitation, $\bar{R}$ is mean molecular rotation time in radians/sec, and $A_o$ is the fluorescence anisotropy in the "frozen" state, in the absence of Brownian rotation. However, if fluorescence anisotropy is measured with steady-state, continuous excitation, A is an average of the time-resolved decay over time weighted by the decay of intensity:

$$A(\tau) = \frac{\int_o^\infty e^{-t/\tau} A(t) dt}{\int_o^\infty e^{-t/\tau} dt} = \frac{1}{\tau} \int_o^\infty e^{-t/\tau} A(t) dt \quad (2)$$

where $\tau$ is the fluorescence lifetime of the fluorophore.

Carrying out the transform results in the Perrin equation:

$$A = \frac{A_o}{1 + 6\bar{R}\tau} \text{ or } \frac{A_o}{A} = 1 + 6\bar{R}\tau \quad (3)$$

which for an ideal spherical molecule becomes:

$$\frac{A_o}{A} = \frac{1 + R_g T}{\eta V} \tau \quad (4)$$

where $R_g$ is the gas constant, T is temperature, $\eta$ is viscosity, and V is the fluorophore's hydrodynamic volume.

Although presented in my pending U.S. Pat. Ser. No. 08/231,191 (Zuckerman) for the specific case of a methodology for the determination of oxygen concentration or partial pressure, one can consider the general case of any fluorophore whose excited state may be quenched, and the concentration of the quencher thereby determined. The quenching of fluorescence lifetime according to the Stern-Volmer relation may be described as follows:

$$\tau = \frac{\tau_o}{1 + K_D[Q]} \quad (5)$$

where [Q] is the concentration of the quencher of a given fluorophore, $K_D$ is the dynamic quench constant, and $\tau_o$ is luminescence lifetime in the absence of quencher. By combining equations 3 and 5, we derive a novel mathematical relationship which formally relates quencher concentration to steady-state luminescence anisotropy:

$$[Q] = \frac{A_o - A(6\bar{R}\tau_o + 1)}{K_D(A - A_o)} \quad (6)$$

As shown below, fluorescence anisotropy is operationally defined, and formally related to quencher concentration by the following equation:

$$A = \frac{I_\parallel G - I_\perp}{I_\parallel G + 2I_\perp} = \frac{A_o(K_D[Q] + 1)}{6\bar{R}\tau_o + K_D[Q] + 1} \quad (7)$$

where $I_\parallel$ and $I_\perp$ are the intensities of fluorescence emission with their electric vectors respectively parallel and perpendicular to that of the linearly polarized exciting radiation, G is an empirical correction factor used to correct for transmission efficiency in the parallel and perpendicular planes, and where additional symbols used in the formal definition of anisotropy are as described above.

Consequently the present invention, although previously presented for the specific case of the quencher dioxygen (pending U.S. Pat. Ser. No. 08/231,191), should be viewed as a general methodology for the determination of the concentration of any quencher of excited states. In practice, the resolution of the technique may be optimized for a given fluorophore and quencher by adjusting the viscosity of the medium, and therefore the rotational velocity of the fluorophore, to the fluorescence lifetime of the fluorophore in the absence of quencher. This may be accomplished for a lipid soluble fluorophore by choosing a lipid of appropriate viscosity, or for a nonlipid soluble fluorophore by conjugating the fluorophore to a carrier molecule of sufficient hydrodynamic volume in a medium whose viscosity is manipulated by adjusting glycerol concentrations in a glycerol-water mixture (1%–100%, w/w) or sucrose concentration in a sucrose-water medium (1%–84%, w/v). Although not meant to be an inclusive list of the classes of fluorophores and quenchers to which the invention may be applied, one might consider the steady-state measurement of pH for the fluorophore fluorescein, or a fluorescein derivative, whose fluorescence lifetime is quenched by protons. Similarly, chloride concentrations may be determined using the same steady-state methodology employing the fluorophore quinine, or the concentration of iodide determined using the fluorophore γ-pyrenebutyric acid. It will then be obvious to one skilled in the art that the general methodology presented herein may be applied for the detection of a host of ion and other quencher concentrations by selecting the appropriate fluorophore-quencher combination and, by manipulating viscosity, thereby adjusting the rotational velocity of the fluorophore to the range of fluorescence lifetimes encountered over the desired quencher concentration range. For example, in the case of lipid soluble fluorophores such as N-(5-fluoresceinthiocarbamoyl)-1,2-dihexadecanoyl-sn-glycero-3-phosphoethanolamine (Molecular Probes. Eugene, Oreg.), liposomes composed of mixtures of phosphatidylethanolamine and phosphatidylcholine may be employed and the viscosity of the lipid layer increased by the addition of cholesterol. The specific ratios employed will depend upon the temperature of the assay medium and the fluorescence lifetime of the specific probe molecule employed.

In addition to the application of the present invention to the determination of the concentrations of quenchers of excited states, the methodology may be further extended to encompass the determination of the concentration of any substance of interest in a sample. In this embodiment of the invention, a fluorophore is conjugated to a larger carrier molecule which has a high affinity for the substance in question. For example, a fluorophore may be conjugated to an antibody raised against an antigenic analyte, employing an amine reactive fluorophore and its conjugation to amine groups on the antibody, according to the conjugation reaction described below. Similarly, a quantity of the substance to be measured is conjugated to a quencher of the excited state of the carrier fluorophore. The fluorescently-labelled substance along with the sample, containing a quantity of the unlabelled substance to be determined, is added to the analysis mixture, resulting in a competition for sites on the carrier molecule. This competition will displace quencher-labelled molecules from the carrier, thereby increasing the fluorescence lifetime of the carrier fluorophore. An increase in the lifetime of the carrier fluorophore will in turn reduce the fluorescence anisotropy of the sample measured at the emission wavelength of the carrier fluorophore. Therefore, in this embodiment of the invention fluorescence anisotropy will decrease with increasing sample concentrations of the substance whose concentration is to be determined. In other words, as the concentration of the substance under analysis is raised the number of quenchers on the carrier is reduced, thus increasing the fluorescence lifetime of the carrier fluorophore (equation 5), thereby increasing the angle swept out by the carrier fluorophore during its lifetime. Fluorescence anisotropy, therefore, decreases with increasing concentration of the substance under measurement.

An interesting choice for the two fluorophores employed in this methodology would represent energy donor and acceptor molecules capable of Förster energy transfer. The basic paradigm of Förster energy transfer involves the excitation of the donor molecule with light of a wavelength lying within the absorption region of the donor. A small amount of the excitation energy is given up to the surroundings in the form of vibrational energy of the molecule (transition to the lowest vibrational state of the electronically excited molecule); the remainder can be given off either through emission of fluorescent light or by energy transfer to the acceptor molecule. The efficiency of the energy transfer depends upon the quantum yield of the donor, the degree of overlap between the emission spectrum of the donor and the absorption spectrum of the acceptor, and the orientation and distance between the donor and acceptor. Depending upon the extent to which the above conditions are met, the approximation of the acceptor and donor molecules in space will result in a shortening of the fluorescence lifetime of the donor fluorophore. When donor-acceptor pairs are used according to the method described above, fluorescence anisotropy measured at the emission wavelength of the donor will decrease with increasing concentration of the measured substance in the sample. A significant advantage of employing Förster energy transfer donor-acceptor pairs is the ability to shift the absorption band of the donor to longer wavelengths, thereby permitting the use of less expensive light sources such as light emitting diodes (LEDs) and laser diodes.

The embodiment of the invention employing energy transfer donor-acceptor pairs will be illustrated by two nonlimiting examples. Consider first a general detection system designed to detect the quantity of a protein. A polyclonal antibody raised against the protein is labelled with FITC (fluorescein isothiocyanate), and thus serves as the donor, while a quantity of the protein is labelled with malachite green isothiocyanate, thereby providing a suitable acceptor. These labelled molecules, along with the unlabelled protein within the sample, are admixed in a glycerol-water buffer to provide the appropriate viscosity. The mixture is illuminated with linearly polarized light at the absorption wavelength for FITC, and the fluorescence anisotropy of the sample determined at the emission wavelength of FITC (donor emission). As the quantity of the unlabelled protein in question increases in the sample it will displace protein labelled with acceptor fluorophores from the carrier, thereby increasing donor fluorescence lifetime. Therefore, the fluorescence anisotropy at the FITC emission band (donor wavelength) will decrease systematically as a function of increasing unlabelled protein concentration in the sample. A specific example of such an assay system would be for the detection of prostatic specific antigen employing an antibody raised against this antigen. The isothiocyanate forms of fluorescein and malachite green may be conjugated respectively to carrier (antibody) and analyte (protein) donor and acceptor pairs by means of the conjugation of these amine reactive probes to amine groups on the carrier and analyte. In brief, the protein in question is dissolved in 0.1M bicarbonate at a concentration of 5–20 mg/ml. The amine reactive isothiocyanate is dissolved in anhydrous dimethylformamide at 10 mg/ml. The reactive dye solution is added slowly to the stirred protein solution, resulting in approximately ⅓ of the reactive dye conjugating to the protein. After one hour of incubation, the reaction is stopped by the addition of hydroxylamine at a final concentration of 0.15M. The conjugate is separated from unbound dye and hydroxylamine by gel filtration on a PD-10 column (Pharmacia, Uppsala, Sweden). In this manner donor and acceptor fluorophores may be easily conjugated to carrier and analyte molecules respectively.

As a second example, consider a system designed to measure blood glucose levels. In this case one might employ concanavalin A (ConA) as the carrier molecule, which has a high affinity for glucose, labelled with Cascade Blue (Molecular Probes, Eugene, Oreg.) as the donor fluorophore and a quantity of fluorophore-labelled glucose such as 6-NBD-glucosamine (6-(N-(7-nitrobenz-2-oxa-1,3-diazol-4-yl)amino)-6-deoxyglucose ) (Molecular Probes, Eugene, Oreg.) as the acceptor. In this system, glucose in the blood will displace fluorescently labelled glucose bound to the carrier thereby resulting in a decrease in the fluorescence anisotropy measured at the Cascade Blue emission band. Although two nonlimiting examples have been provided it will be obvious to one skilled in the art that the basic method disclosed herein may be adapted to determine the concentrations of a host of substances such as saccharides, DNA fragments, hormones, drugs, and immunoglobulins, to name a few.

The present invention has all of the advantages of a direct, time-resolved fluorescence lifetime system, without the need for intense, pulsed laser excitation and its potentially damaging effects on the imaged specimen. In addition, the cumbersome and expensive equipment required to measure fluorescence decays in the nanosecond range are avoided. Similarly, since steady-state, continuous fluorescence anisotropy determinations are the time average of a huge number of fluorescence decay events, such steady-state measurements must be more precise than any time-resolved procedure. Moreover, the steady-state procedure will be equally accurate and precise at short and long fluorescence lifetimes, unlike time-resolved methodologies which lose accuracy as the fluorescence lifetime approaches the duration of the excitation pulse. The present invention determines analyte concentration by measurement of steady-state fluorescence anisotropy, while in U.S. Pat. No. 4,476,870 (Peterson) as well as U.S. Pat. No. 5,186,173 (Zuckerman), fluorescence intensity is the variable measured. Furthermore, the present invention differs from the inventions disclosed in U.S. Pat. No. 5,039,219 (James et. al. ) as well as U.S. Pat. No. 5,317,162 (Pinsky et. al.) and U.S. Pat. No. 5,281,825 (Berndt et. al.) in that all of these patents employ time-resolved methods, whether by pulse or phase modulation fluorometry. In the present invention, an indirect, steady-state measure of luminescence lifetime, viz. luminescence anisotropy, is employed in simple-to-implement configurations to provide measurements of the concentrations of a host of analytes of biologic and physical import, in vivo and in vitro, without the limitations of the prior art.

FIG. 1 is a schematic of an apparatus 10 designed for the topographic mapping of tissue and blood analyte concentration in an imaged tissue. The tissue 12, containing the analyte and probe substance, is illuminated with nonpolarized visible light by a fiberoptic illuminator 14 utilizing a tungsten source 16. The radiant energy of a xenon arc lamp 18 is gathered by a collector lens 20, is shuttered by a shutter 22, and passes through a Glan-Thompson polarizer 24 (Ealing, Inc.). The light is spectrally shaped by an excitation filter 26 and is then reflected by a dichroic mirror 28 (Omega Optical) which reflects excitation wavelengths through an objective lens 30 to the imaged tissue. Emitted luminescence from the excited tissue 12 is gathered by the objective lens 30 and passes through the dichroic mirror 28, and through an emission filter 32, which passes emission wavelengths to a Wollaston prism polarizer 34 which resolves the emitted fluorescence into its linearly polarized components parallel 36 and perpendicular 38 to the plane of excitation polarization. The vector components ($I_\parallel$ and $I_\perp$) are respectively and simultaneously detected by the CCD (charge coupled devices) chips of two video cameras 40A and 40B (e.g. Xybion model 250). It is obvious to one skilled in the art that alternative optical detectors with sufficient spatial resolution, such as slow scan chilled CCD cameras, SIT or ISIT tube cameras, or photodiode arrays (not shown) would also be suitable for the detection of the two-dimensional distributions of the parallel and perpendicular components of the emitted fluorescence. The outputs of the two video cameras are digitized by two digitizing boards 42A and 42B (such as sold by Imaging Technologies or under the designation model DT3851 by Data Translation)within a microcomputer 44, (e.g., an IBM® or clone computer, preferably having a processing chip operating at 33 or 66 MHz). Such a device is sufficient for the task and for subsequent image processing prior to display on the monitor 46.

Figure 2:
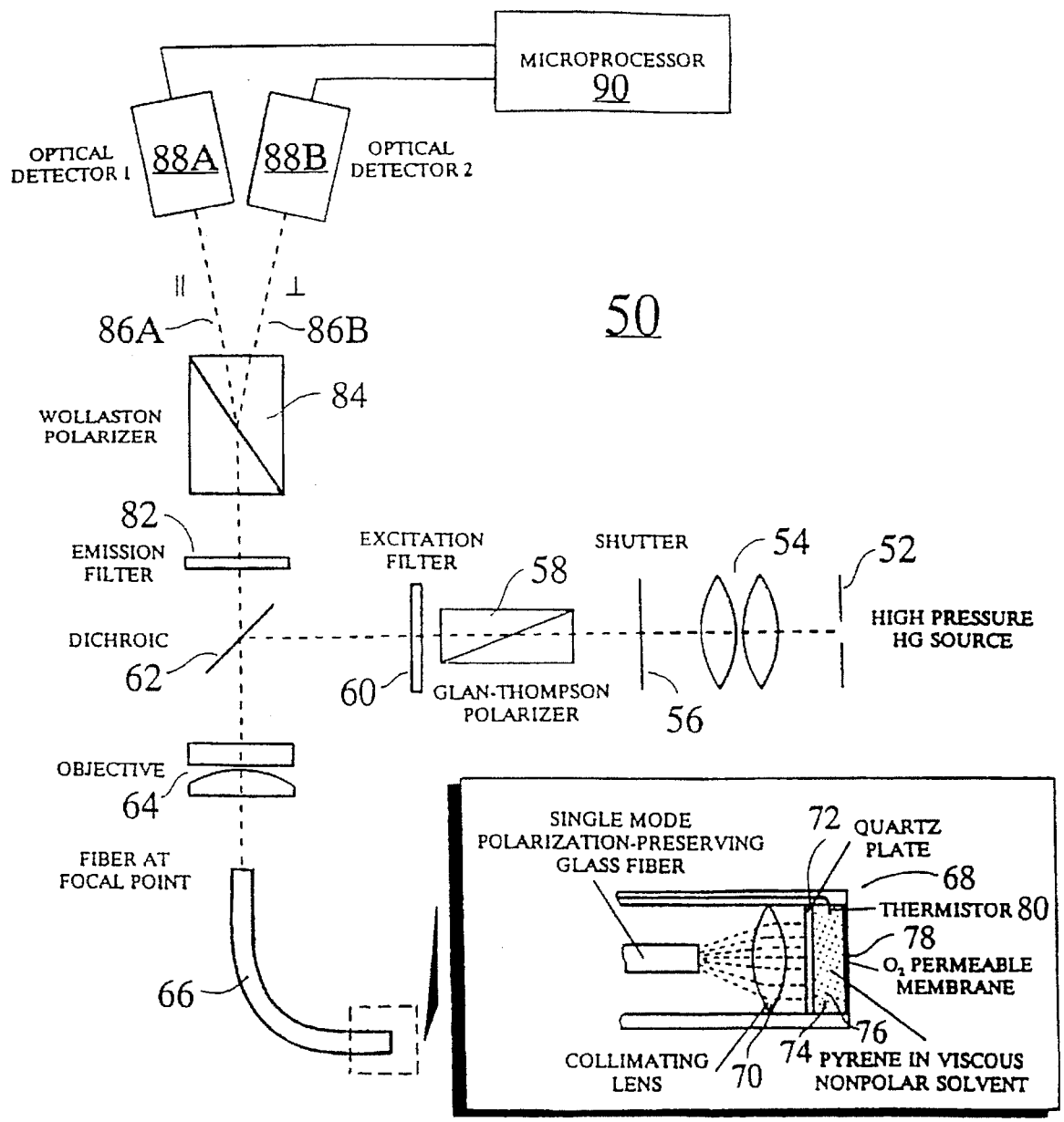
FIG. 2 is an apparatus of the present invention used to measure the analyte concentration of a fluid contacting the tip of a sealed fiber optic catheter.

FIG. 2 shows an apparatus 50 constructed in accordance with the present invention to implement the indirect fluorescence lifetime system in a sealed catheter design which does not require calibration prior to its every usage. As in the previous embodiment the radiant energy of a xenon arc lamp 52 is gathered by a collector lens 54, is shuttered via shutter 56, and passes through a Glan-Thompson polarizer 58 (such as sold by Ealing, Inc. under the designation of catalog number 34-5223). The light is spectrally shaped by an excitation filter 60 and is then reflected by a dichroic mirror 62 (such as sold by Omega Optical) which reflects excitation wavelengths through an objective lens 64. A single mode polarization-preserving glass fiber 66 (such as sold by Ealing, Inc., under the designation model HB450) is fixed at the focal point of the objective lens. The core diameter of such fibers is typically <10 microns, thereby permitting an exceedingly narrow catheter to be designed. In the case of a narrow submillimeter catheter, the linearly polarized light passes directly to the analyte-sensitive tip 68, whereas for larger diameter catheters the glass fiber 66 is mounted at the focal point of a collimating lens 70 which is used to provide uniform illumination of the catheter tip 68. The sealed analyte-sensitive tip 68 contains a quartz plate 72 which separates the optical components from the viscous medium 74 in the tip 68. The analyte-quenchable probe substance dissolved in a viscous medium is sealed within the catheter by an analyte permeable membrane 78. A micro-thermistor 80 is also incorporated into the tip 68 of the catheter to allow simultaneous measurement of temperature, thus permitting temperature corrections to be performed according to the relation described in equation 4. Since optics are reversible, the linearly polarized fluorescence emission from the probe tip 68 returns along the single mode polarization-preserving glass fiber and is collected by the objective lens 64. Emission wavelengths pass through the dichroic mirror 62 and wavelengths are further selected by an emission filter 82 which passes these emission wavelengths to a Wollaston prism polarizer 84, which resolves the emitted fluorescence into its linearly polarized components parallel 86A and perpendicular 86B to the plane of excitation polarization. The vector components ($I_\parallel$ and $I_\perp$) are respectively and simultaneously detected by two optical detectors 88A and 88B, which can be photodiodes or photomultiplier tubes.

Once the relations and constants employed in the previously described equations are determined, they may be fixed and employed in every catheter manufactured, and each catheter need not be individually calibrated at the factory, or calibrated prior to its use in a clinical situation. This represents the considerable advantage of the present catheter design over previous designs which require constant recalibration in the factory as well as in the field.

EXAMPLE

To measure the topographic distribution of tissue $PO_2$ in retinal tissue, an imaging apparatus was set up as follows and as schematically illustrated in FIG. 1. A bovine eye was obtained from a local slaughterhouse and transported on ice to the laboratory. The isolated bovine eye was set up for normothermic arterial perfusion according to the procedures of de Coo, Zonnenberg and Trap (*Current Eye Research*, 12(4), 293–301, 1993), using oxygenated serum-free MEM (minimal essential medium) which was initially supplemented with 108 μM sodium pyrenebutyrate. After one hour of perfusion with MEM containing sodium pyrenebutyrate, the biocompatible, fluorescent probe substance reached equilibrium concentration in the retinal tissue, and the eye was subsequently perfused with oxygenated MEM alone during the period of time in which measurements of tissue $PO_2$ were performed. Corneal refraction was negated by a custom fundus lens made of UV transmitting glass (Optical Industries), and the retina was imaged first in visible light and a region of the retina selected which contained a retinal arteriole. Once proper orientation was established visible light was discontinued, and the retinal tissue was illuminated with linearly polarized ultraviolet light (UV). The radiant energy of a high pressure mercury bulb was gathered by a collector lens, was shuttered, and passed through a Glan-Thompson polarizer (Ealing, Inc.). The UV light was spectrally shaped by an excitation filter (340 nm peak, 25 nm half bandpass) and was then reflected by a dichroic mirror (Omega Optical) which reflects wavelengths <400 nm through an objective lens to the imaged retinal tissue. Emitted fluorescence (wavelengths >400 nm) from the excited tissue was gathered by the objective lens and passed through the dichroic mirror, and through an emission filter, which passed wavelengths from 400–420 nm to a Wollaston prism polarizer which resolved the emitted fluorescence into its linearly polarized components parallel and perpendicular to the plane of excitation polarization. The vector components ($I_\parallel$ and $I_\perp$) were respectively and simultaneously detected by the CCD (charge coupled devices) chips of two video cameras (Xybion model 250).

The vector components of fluorescence emission parallel and perpendicular to the plane of excitation polarization were digitized by the previously identified two digitizing boards within the previously identified computer operating at 66 MHz, and stored to hard disk (not shown). Computer software was run on the computer to allow the variation of the slopes and offsets at each pixel location within the CCD arrays to be corrected by a correction file in the software, thereby ensuring uniform responsivity across the detector array. Similarly, the software allowed anisotropy to be calculated at a plurality of locations by means of equation 7 and converted to a two dimensional representation of tissue $PO_2$ by the application of equation 6 at each pixel locus. This procedure allowed the gathering of more than 300,000 values of retinal tissue $PO_2$ in space within approximately 33 milliseconds. The values for the constants used in equation 6 were previously determined during calibration experiments which involved the simultaneous measurement of tissue $PO_2$ by an oxygen microelectrode and by the indirect lifetime (anisotropy) system.

Figure 3A:
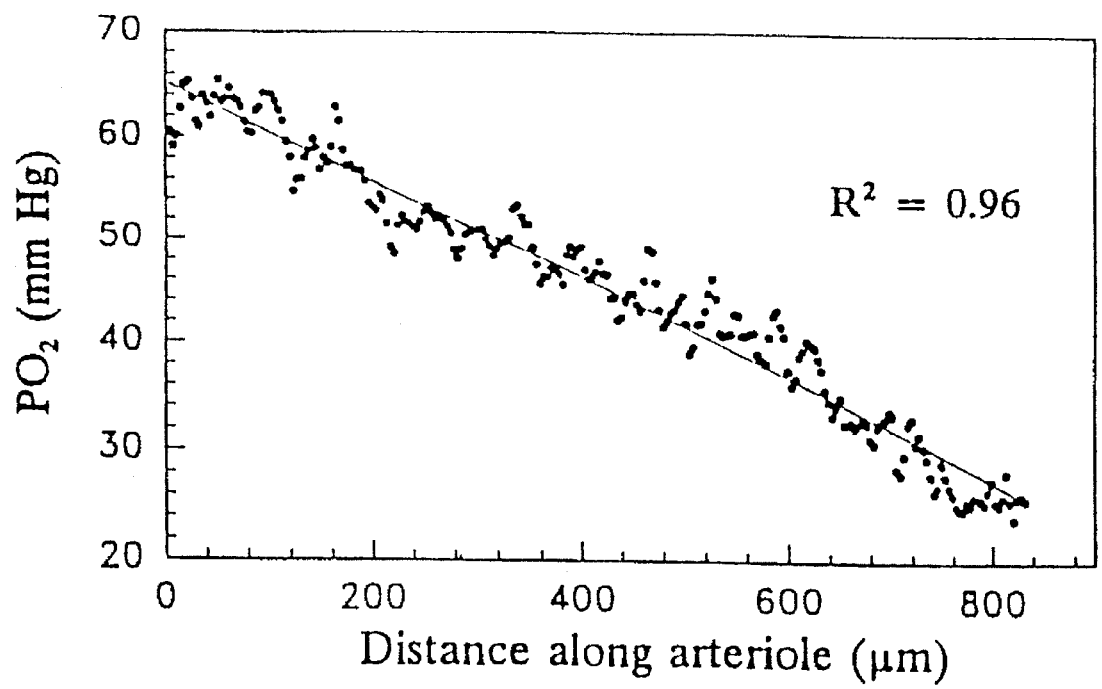
FIG. 3A is a graphical illustration of $PO_2$ levels measured parallel to a retinal arteriole within the retina of an isolated and perfused bovine eye, the longitudinal $PO_2$ drop parallel to the arteriole being fit to the function $\Delta PO_2 \alpha M/(VD^2)$, the coefficient of determination being $R^2$.
Figure 3B:
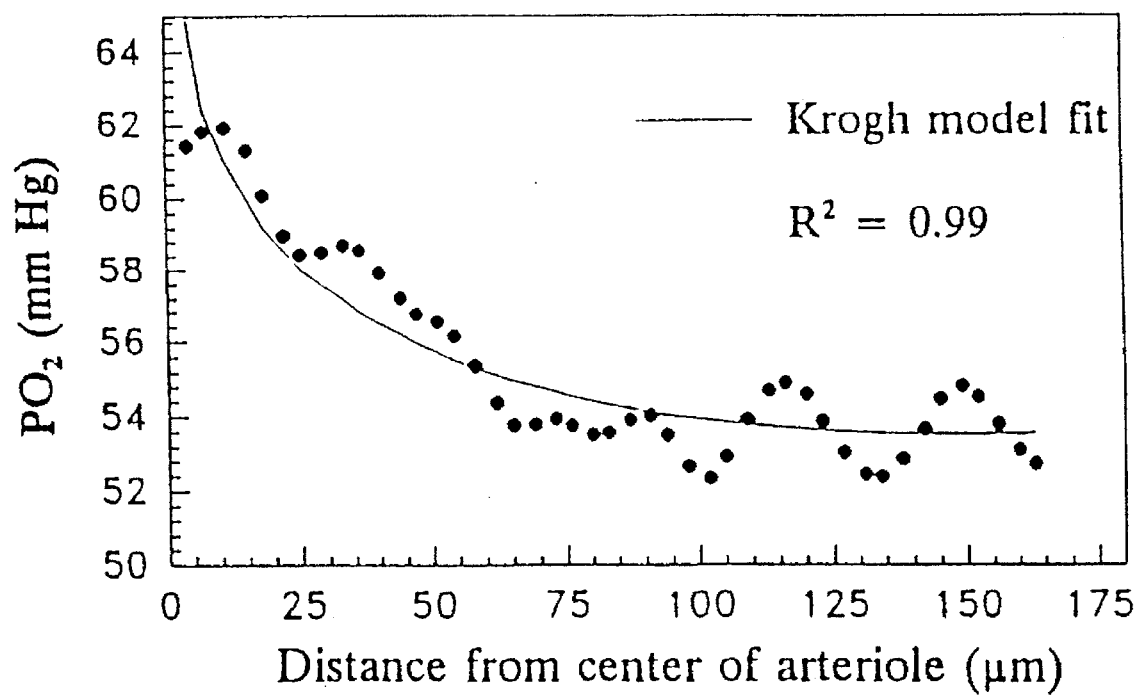
FIG. 3B is a graphical illustration of $PO_2$ levels measured perpendicular to a retinal arteriole within the retina of an isolated and perfused bovine eye, the $PO_2$ level perpendicular to the arteriole being fit to the Krogh mathematical model, the coefficient of determination being $R^2$.

To test the validity and precision of the system and the resultant optical map of retinal tissue $PO_2$, $PO_2$ gradients were measured both parallel and perpendicular to the retinal arteriole, as the mathematical functions describing these relationships can be predicted from oxygen diffusion mathematics, and are well established in the literature. The results of these measurements are shown in FIGS. 3A and 3B. Oxygen diffusion mathematics predicts that the longitudinal $PO_2$ drop in the tissue parallel to the arteriole should follow a linear relationship, whose slope is directly proportional to the oxygen consumption rate of the tissue (M) and inversely proportional to the velocity (V) of oxygen-containing solution within the arteriole times the square of the arteriolar diameter (D). As shown in FIG. 3A the tissue $PO_2$ measurements along the length of the arteriole conform excellently to this well-established linear relationship, with a coefficient of determination ($R^2$) for a linear fit of 0.96 obtained; i.e., 96% of the variance in the data is accounted for by the expected linear fit. Similarly, the $PO_2$ gradient perpendicular to an arteriole should conform to a monotonically decreasing function which is described mathematically by the Krogh model. In FIG. 3B a Krogh model fit has been applied to the data with a goodness of fit ($R^2$) of 0.99; i.e., 99% of the variance in the data is accounted for by the expected mathematical relation. The data of FIGS. 3A and 3B, then, demonstrate that the indirect fluorescence lifetime system provides a noninvasive and valid method for evaluating tissue $PO_2$ in space and time.

While the present invention has been described in conjunction with preferred embodiments and illustrative examples, one skilled in the art after reading the foregoing specifications will be able to effect various changes, substitutions, and other alterations to the methods set forth herein.

I claim:

1. A method of measuring concentration of an analyte in a medium, the method comprising the steps of:
   a) introducing, into the medium, a probe substance which becomes luminescent when irradiated and whose luminescence is quenched by the analyte in the medium,
   b) irradiating the medium with linearly polarized light so as to cause the probe substance to become luminescent,
   c) resolving luminescence emitted by the probe substance into vector components parallel and perpendicular to a plane of polarization of said linearly polarized light,
   d) calculating a luminescence anisotropy, as a function of said vector components, in space or in time, of the irradiated medium, and
   e) applying a mathematical function which relates said luminescence anisotropy to said concentration of the analyte in said medium, the mathematical function being in the form of an equation.

2. The method of claim 1, further comprising the step of calculating a luminescence lifetime of the probe substance according to the following equation:

$$\tau = \frac{\tau_o}{1 + K_D[Q]}$$

wherein $\tau$ is the luminescence lifetime, is the concentration of the analyte, $K_D$ is a dynamic quench constant, and $\tau_o$ is a luminescence lifetime in the absence of analyte.

3. The method of claim 1, further comprising the step of selecting the equation as follows:

$$[Q] = \frac{A_o - A(6\bar{R}\tau_o + 1)}{K_D(A - A_o)}$$

wherein A is fluorescence anisotropy, defined as $$A = \frac{I_\parallel G - I_\perp}{I_\parallel G + 2I_\perp}$$

wherein $I_\parallel$ and $I_\perp$ are intensities of luminescence emission with their electric vectors respectively parallel and perpendicular to the linearly polarized light of step (b), G is an empirical correction factor used to correct for transmission efficiency in parallel and perpendicular planes, $\bar{R}$ is mean molecular rotation time in radians/sec, $A_o$ is fluorescence anisotropy in a "frozen" state, in the absence of Brownian rotation, $K_D$ is a dynamic quench constant, $\tau_o$ is luminescence lifetime in the absence of quencher, and is the concentration of the analyte which is to be determined.

4. The method of claim 1, further comprising the step of determining a topographic distribution of said analyte concentration in said medium.

5. The method of claim 1, wherein the probe substance is disposed in an optical sensor which comprises a tip and a thermistor, the method further comprising the step of correcting anisotropy measurements for temperature of the tip of the sensor according to the following equation:

$$\frac{A_o}{A} = \frac{1+R_gT}{\eta V} \tau$$

wherein $R_g$ is a gas constant, T is temperature, $\eta$ is viscosity, V is hydrodynamic volume of the probe substance, A is luminescence anisotropy, $A_o$ is a luminescence anisotropy in a "frozen" state, in the absence of Brownian rotation, and $\tau$ is a fluorescence lifetime.

6. The method of claim 1, further comprising the step of determining tomographically a topographic distribution of said analyte concentration within the medium by means of optical serial sectioning methodologies.

7. A method of measuring concentration of an analyte in a medium, the method comprising the steps of:
 a) conjugating probe molecules to a carrier which has an affinity for the analyte, and adding the carrier to the medium, wherein the probe molecules are chosen such that they become luminescent when irradiated,
 b) adding to the medium a quantity of the analyte conjugated with a substance selected from the group consisting of a quencher of luminescence energy of the probe molecules and an energy transfer acceptor of luminescence energy of the probe molecules,
 c) irradiating the medium with linearly polarized light so as to cause the probe molecules to become luminescent,
 d) resolving luminescence emitted by the probe molecules into vector components parallel and perpendicular to a plane of polarization of said linearly polarized light,
 e) calculating a luminescence anisotropy, as a function of said vector components, in space or in time, of the irradiated medium, and
 f) applying an empirically determined mathematical function which relates said luminescence anisotropy to said concentration of analyte in said medium.

8. The method of claim 7, wherein the luminescence anisotropy (A) of step (e) is defined as:

$$A = \frac{I_\| G - I_\perp}{I_\| G + 2I_\perp}$$

wherein $I_\|$ and $I_\perp$ are intensities of luminescence emission with their electric vectors respectively parallel and perpendicular to the linearly polarized light of step (c), and G is an empirical correction factor used to correct transmission efficiency in parallel and perpendicular planes.

9. The method of claim 7, further comprising the step of determining a topographic distribution of said analyte concentration in said medium.

10. The method of claim 7, wherein the probe molecules are disposed in an optical sensor which comprises a tip and a thermistor, the method further comprising the step of correcting anisotropy measurements for temperature of the tip of the sensor by means of an empirically determined mathematical function.

11. The method of claim 7, further comprising the step of determining tomographically a topographic distribution of said analyte concentration within the medium by means of optical serial sectioning methodologies.

12. A method of measuring concentration of an analyte in a medium, the method comprising the steps of:
 a) conjugating probe molecules to a carrier which has an affinity for the analyte, and adding the carrier to the medium, wherein the probe molecules are chosen such that they become luminescent when irradiated,
 b) adding to the medium a known quantity of the analyte conjugated with a substance selected from the group consisting of a quencher of luminescence energy of the probe molecules and an energy transfer acceptor of luminescence energy of the probe molecules,
 c) adding to the medium a sample to be analyzed which contains an unknown quantity of the analyte,
 d) irradiating the medium with linearly polarized light so as to cause the probe molecules to become luminescent,
 e) resolving luminescence emitted by the probe molecules into vector components parallel and perpendicular to a plane of polarization of said linearly polarized light,
 f) calculating a luminescence anisotropy, as a function of said vector components, in space or in time, of the irradiated medium, and
 g) applying an empirically determined mathematical function which relates said luminescence anisotropy to said concentration of the unknown quantity of analyte in said medium.

13. The method of claim 12, wherein the luminescence anisotropy (A) of step (f) is defined as:

$$A = \frac{I_\| G - I_\perp}{I_\| G + 2I_\perp}$$

wherein $I_\|$ and $I_\perp$ are intensities of luminescence emission with their electric vectors respectively parallel and perpendicular to the linearly polarized light of step (d), and G is an empirical correction factor used to correct transmission efficiency in parallel and perpendicular planes.

14. The method of claim 12, further comprising the step of determining a topographic distribution of said analyte concentration in said medium.

15. The method of claim 12, wherein the probe molecules are disposed in an optical sensor which comprises a tip and a thermistor, the method further comprising the step of correcting anisotropy measurements for temperature of the tip of the sensor by means of an empirically determined mathematical function.

16. The method of claim 12, further comprising the step of determining tomographically a topographic distribution of said analyte concentration within the medium by means of optical serial sectioning methodologies.

17. Apparatus for measuring a concentration of an analyte, comprising:
 a) means for directing polarized light to an optical sensor,
 b) the optical sensor comprising means for housing a probe substance which becomes luminescent when irradiated with light, the probe substance being chosen such that its luminescence is quenched by the analyte,
 c) means for resolving said luminescence, emitted by the probe substance, into vector components parallel and perpendicular to a plane of polarization of said polarized light, and for detecting intensities of said vector components, and
 d) means for processing the intensities obtained from the resolving and detecting means, the processing means comprising means for calculating said concentration of the analyte based on values of said intensities.

18. The apparatus of claim 17, wherein the optical sensor contains a viscous medium, the probe substance and the viscous medium being separated from the analyte by a membrane permeable to the analyte.

19. The apparatus of claim 17, wherein the calculating means comprises means for calculating analyte concentration according to the following equation:

$$[Q] = \frac{A_o - A(6\bar{R}\tau_o + 1)}{K_D(A - A_o)}$$

wherein A is fluorescence anisotropy, defined as $$A = \frac{I_{\|}G - I_{\perp}}{I_{\|}G + 2I_{\perp}}$$

wherein $I_{\|}$ and $I_{\perp}$ are intensities of luminescence emission with their electric vectors respectively parallel and perpendicular to the polarized light originating from the directing means, G is an empirical correction factor used to correct for transmission efficiency in parallel and perpendicular planes, $\bar{R}$ is mean molecular rotation time in radians/sec, $A_o$ is fluorescence anisotropy in a "frozen" state, in the absence of Brownian rotation, $K_D$ is a dynamic quench constant, $\tau$ is a luminescence lifetime in the absence of quencher, and is the concentration of the analyte which is to be determined.

20. The apparatus of claim 17, wherein the analyte is disposed in a medium, the apparatus further comprising means for determining a topographic distribution of said analyte concentration in said medium.

21. The apparatus of claim 17, wherein the optical sensor comprises a tip and a thermistor, the apparatus further comprising means for correcting anisotropy measurements for temperature of the tip of the sensor according to the following equation:

$$\frac{A_o}{A} = \frac{1 + R_g T}{\eta V} \tau$$

wherein $R_g$ is a gas constant, T is temperature, $\eta$ is viscosity, V is hydrodynamic volume of the probe substance, A is luminescence anisotropy, $A_o$ is a luminescence anisotropy in a "frozen" state, in the absence of Brownian rotation, and $\tau$ is a fluorescence lifetime.

22. Apparatus for measuring concentration of an analyte, comprising:
  a) means for directing polarized light to an optical sensor,
  b) the optical sensor comprising means for housing a carrier with a high affinity for the analyte, the carrier being conjugated to probe molecules that become luminescent when irradiated, the optical sensor also housing a known quantity of the analyte conjugated to a substance selected from the group consisting of a quencher of luminescence energy of the probe molecules and an energy transfer acceptor of luminescence energy of the probe molecules,
  c) the optical sensor being disposed in a medium which contains an unconjugated form of the analyte,
  d) means for resolving said luminescence, emitted by the carrier probe molecules, into vector components parallel and perpendicular to a plane of polarization of said polarized light, and for detecting intensities of said vector components, and
  e) means for processing the intensities obtained from the resolving and detecting means, the processing means comprising means for calculating a concentration of the unconjugated form of the analyte contacted by the optical sensor, based on values of said intensities.

23. The apparatus of claim 22, wherein the optical sensor contains a viscous medium containing the carrier and the conjugated analyte, the carrier and the conjugated analyte being separated from the unconjugated form of the analyte by a membrane permeable to the analyte in its unconjugated form but impermeable to the conjugated analyte.

24. The apparatus of claim 22, the apparatus further comprising means for determining a topographic distribution of said analyte concentration in said medium.

25. The apparatus of claim 22, wherein the optical sensor comprises a tip and a thermistor, the apparatus further comprising means for correcting anisotropy measurements for temperature of the tip of the sensor by an empirically determined mathematical function.

26. The apparatus of claim 22, the apparatus further comprising means for determining a spatial distribution of said analyte concentration within the medium.

27. Apparatus for measuring concentration of an analyte disposed in a medium, the apparatus comprising:
  a) means for directing polarized light towards the medium,
  b) the medium including a probe substance which becomes luminescent when irradiated with light, the probe substance being chosen such that its luminescence is quenched by the analyte,
  c) means for resolving said luminescence, emitted by the probe substance, into vector components parallel and perpendicular to a plane of polarization of said polarized light, and for detecting intensities of said vector components, and
  d) means for processing the intensities obtained from the resolving and detecting means, the processing means comprising means for calculating said concentration of the analyte based on values of said intensities.

28. The apparatus of claim 27, wherein the calculating means comprises means for calculating said analyte concentration according to the following equation:

$$[Q] = \frac{A_o - A(6\bar{R}\tau_o + 1)}{K_D(A - A_o)}$$

wherein A is fluorescence anisotropy, defined as $$A = \frac{I_{\|}G - I_{\perp}}{I_{\|}G + 2I_{\perp}}$$

wherein $I_{\|}$ and $I_{\perp}$ are intensities of luminescence emission with their electric vectors respectively parallel and perpendicular to the polarized light originating from the directing means, G is an empirical correction factor used to correct for transmission efficiency in parallel and perpendicular planes, $\bar{R}$ is mean molecular rotation time in radians/sec, $A_o$ is a fluorescence anisotropy in a "frozen" state, in the absence of Brownian an rotation, $K_D$ is a dynamic quench constant, $\tau$ is a luminescence lifetime in the absence of quencher, and is the concentration of the analyte which is to be determined.

29. The apparatus of claim 27, the apparatus further comprising means for determining a topographic distribution of said analyte concentration in the medium.

30. The apparatus of claim 27, further comprising means for correcting anisotropy measurements for temperature according to the following equation:

$$\frac{A_o}{A} = \frac{1 + R_g T}{\eta V} \tau$$

wherein $R_g$ is a gas constant, T is temperature, $\eta$ is viscosity, V is hydrodynamic volume of the probe substance, A is luminescence anisotropy, $A_o$ is luminescence anisotropy in a "frozen" state, in the absence of Brownian rotation, and $\tau$ is fluorescence lifetime.

31. The apparatus of claim 27, the apparatus further comprising means for determining tomographically a topographic distribution of said analyte concentration within the medium by means of optical serial sectioning methodologies.

32. Apparatus for measuring concentration of an analyte disposed in a medium, the apparatus comprising:

a) means for directing polarized light towards the medium, b) the medium including carriers conjugated with probe molecules which become luminescent when irradiated with light, the medium also including a known quantity of the analyte conjugated with substances selected from the group consisting of a quencher of luminescence energy of the probe molecules and an energy transfer acceptor of luminescence energy of the probe molecules, c) means for resolving said luminescence, emitted by the probe molecules, into vector components parallel and perpendicular to a plane of polarization of said polarized light, and for detecting intensities of said vector components, and d) means for processing the intensities obtained from the resolving and detecting means, the processing means comprising means for calculating said concentration of the analyte based on values of said intensities.

33. The apparatus of claim 32, wherein the calculating means comprises means for calculating said analyte concentration according to an empirically determined mathematical function.

34. The apparatus of claim 32, the apparatus further comprising means for determining a topographic distribution of said analyte concentration in the medium.

35. The apparatus of claim 32, further comprising means for correcting anisotropy measurements for temperature of the medium according to an empirically determined function.

36. The apparatus of claim 32, further comprising means for determining tomographically a topographic distribution of said analyte concentration within the medium by means of optical serial sectioning methodologies.

\* \* \* \* \*

UNITED STATES PATENT AND TRADEMARK OFFICE
CERTIFICATE OF CORRECTION

PATENT NO. : 5,626,134
DATED : May 6, 1997
INVENTOR(S) : Ralph Zuckerman

It is certified that error appears in the above-identified patent and that said Letters Patent is hereby corrected as shown below:

| | DELETE | INSERT |
|---|---|---|
| col.4, l. 3 | $\dfrac{A_o}{A} = \dfrac{1 + R_g T}{\eta V}\tau$ | $\dfrac{A_o}{A} = 1 + \dfrac{R_g T}{\eta V}\tau$ |
| col.4, l. 35 | "where $I_\blacksquare$ and ..." | --where $I_{\parallel}$ and ...-- |
| col. 7, l. 54 | "... components ($I_\blacksquare$ and ..." | --... components ($I_{\parallel}$ and ..-- |
| col. 8, l. 44 | "... components ($I_\blacksquare$ and ..." | --... components ($I_{\parallel}$ and ..-- |
| col. 9, l. 26 | "nents ($I_\blacksquare$ and ..." | --nents ($I_{\parallel}$ and ...-- |
| col. 10, l. 41 | "... lifetime, is the ..." | --... lifetime, [Q] is the ..-- |
| col. 10, l. 55 | "wherein $I_\blacksquare$ and ..." | --wherein $I_{\parallel}$ and ...-- |
| col. 10, l. 62 | "... $\tau_o$ is lumines-" | --... $\tau_o$ is a lumines--- |
| col. 10, l. 63 | "... quencher, and is ..." | --... quencher, and [Q] is ..-- |

UNITED STATES PATENT AND TRADEMARK OFFICE
CERTIFICATE OF CORRECTION

PATENT NO. : 5,626,134
DATED : May 6, 1997
INVENTOR(S) : Ralph Zuckerman

It is certified that error appears in the above-identified patent and that said Letters Patent is hereby corrected as shown below:

| | DELETE | INSERT |
|---|---|---|
| col. 11, l. 7 | $"\dfrac{A_o}{A} = \dfrac{1 + R_g T}{\eta V}\tau"$ | $\dfrac{A_o}{A} = 1 + \dfrac{R_g T}{\eta V}\tau$ |
| col. 11, l. 48 | "wherein $I_\blacksquare$ and ..." | --wherein $I_{\parallel}$ and ...-- |
| col. 12, l. 31 | "wherein $I_\blacksquare$ and ..." | --wherein $I_{\parallel}$ and ...-- |
| col. 13, l. 16 | "wherein $I_\blacksquare$ and ..." | --wherein $I_{\parallel}$ and ...-- |
| col. 13, l. 23 | "... constant, $\tau$ is a" | --... constant, $\tau_o$ is a-- |
| col. 13, l. 24 | ".. quencher, and is" | --.. quencher, and [Q] is-- |

UNITED STATES PATENT AND TRADEMARK OFFICE
CERTIFICATE OF CORRECTION

PATENT NO. : 5,626,134
DATED : May 6, 1997
INVENTOR(S) : Ralph Zuckerman

It is certified that error appears in the above-identified patent and that said Letters Patent is hereby corrected as shown below:

| | DELETE | INSERT |
|---|---|---|
| col. 13, l. 35 | $"\dfrac{A_o}{A} = \dfrac{1 + R_g T}{\eta V}\tau"$ | $--\dfrac{A_o}{A} = 1 + \dfrac{R_g T}{\eta V}\tau--$ |
| col. 14, l. 51 | "wherein $I_\blacksquare$ and . . ." | --wherein $I_{||}$ and . . .-- |
| col. 14, l. 58 | ". . . constant, $\tau$ is" | --. . . constant, $\tau_o$ is-- |
| col. 14, l. 59 | ". . . quencher, and is . . ." | --. . quencher, and [Q] is . .-- |
| col. 15, l. | $"\dfrac{A_o}{A} = \dfrac{1 + R_g T}{\eta V}\tau"$ | $--\dfrac{A_o}{A} = 1 + \dfrac{R_g T}{\eta V}\tau--$ |

Signed and Sealed this

Seventh Day of April, 1998

BRUCE LEHMAN

*Attest:*

*Attesting Officer*   *Commissioner of Patents and Trademarks*